US011738763B2

(12) United States Patent
Hutchings et al.

(10) Patent No.: US 11,738,763 B2
(45) Date of Patent: Aug. 29, 2023

(54) FATIGUE MONITORING SYSTEM FOR DRIVERS TASKED WITH MONITORING A VEHICLE OPERATING IN AN AUTONOMOUS DRIVING MODE

(71) Applicant: WAYMO LLC, Mountain View, CA (US)

(72) Inventors: Keith Hutchings, San Francisco, CA (US); Ilmo van der Lowe, Fremont, CA (US); Vasily Starostenko, San Jose, CA (US); Ganesh Balachandran, Mountain View, CA (US); Andrew Warren, Mountain View, CA (US)

(73) Assignee: Waymo LLC, Mountain View, CA (US)

( * ) Notice: Subject to any disclaimer, the term of this patent is extended or adjusted under 35 U.S.C. 154(b) by 269 days.

(21) Appl. No.: 17/167,289

(22) Filed: Feb. 4, 2021

(65) Prior Publication Data

US 2021/0291839 A1    Sep. 23, 2021

Related U.S. Application Data

(60) Provisional application No. 62/991,124, filed on Mar. 18, 2020.

(51) Int. Cl.
*B60W 50/04* (2006.01)
*A61B 5/18* (2006.01)
*B60W 40/08* (2012.01)

(52) U.S. Cl.
CPC .............. *B60W 50/04* (2013.01); *A61B 5/18* (2013.01); *B60W 2040/0827* (2013.01); *B60W 2540/229* (2020.02); *B60W 2540/26* (2013.01)

(58) Field of Classification Search
None
See application file for complete search history.

(56) References Cited

U.S. PATENT DOCUMENTS

| 8,075,484 B2 | 12/2011 | Moore-Ede |
| 2007/0225882 A1* | 9/2007 | Yamaguchi ........... B60W 50/14 701/45 |

(Continued)

FOREIGN PATENT DOCUMENTS

| KR | 20190095199 A | 8/2019 |
| KR | 20190111318 A | 10/2019 |
| WO | 2019094719 A1 | 5/2019 |

OTHER PUBLICATIONS

International Search Report and Written Opinion for Application No. PCT/US21/22544 dated Jun. 28, 2021.

*Primary Examiner* — Thomas S McCormack
(74) *Attorney, Agent, or Firm* — Botos Churchill IP Law

(57) ABSTRACT

Aspects of the disclosure relate to models for estimating the likelihood of fatigue in test drivers. In some instances, training data including videos of the test drivers while such test drivers are tasked with monitoring driving of a vehicle operating in an autonomous driving mode may be identified. The training data also includes driver drowsiness values generated from one or more human operators observing the videos. The training inputs and outputs may be used to train the model such that when a new video of a first test driver is input into the model, the model will output an estimate of a likelihood of fatigue for that test driver.

20 Claims, 8 Drawing Sheets

(56) References Cited

U.S. PATENT DOCUMENTS

| | | |
|---|---|---|
| 2010/0214105 A1* | 8/2010 | Manotas, Jr. ............ A61B 5/18 |
| | | 348/148 |
| 2014/0139655 A1 | 5/2014 | Mimar |
| 2016/0270718 A1 | 9/2016 | Heneghan et al. |
| 2016/0353995 A1 | 12/2016 | Oleson et al. |
| 2019/0370580 A1* | 12/2019 | Aoi ...................... G06N 3/0454 |
| 2020/0198644 A1 | 6/2020 | Hutchings et al. |
| 2020/0276978 A1* | 9/2020 | Satou ...................... G08G 1/16 |

* cited by examiner

FIGURE 6

FATIGUE MONITORING SYSTEM FOR DRIVERS TASKED WITH MONITORING A VEHICLE OPERATING IN AN AUTONOMOUS DRIVING MODE

CROSS REFERENCE TO RELATED APPLICATIONS

The present application claims the benefit of the filing date of U.S. Provisional Application No. 62/991,124, filed Mar. 18, 2020, the entire disclosure of which is incorporated by reference herein.

BACKGROUND

Autonomous vehicles, such as vehicles which do not require a human driver when operating in an autonomous driving mode, may be used to aid in the transport of passengers or items from one location to another. Testing of these vehicles typically involves a "test driver" who is tasked with monitoring the autonomous vehicle to ensure that the vehicle is operating safely. For instance, a person may be expected to monitor the vehicle and the vehicle's environment while the vehicle operates in the autonomous driving mode and to be ready to take control of the vehicle should the vehicle not be responding appropriately. Supervision of such vehicles is known to increase a person's susceptibility to fatigue, whether due to sleep deprivation, poor quality sleep, fatigue induced by the task itself, or the interaction of these contributing sources of fatigue. Furthermore, as the performance of autonomous vehicles improve, fewer interventions are by a human driver, the likelihood of fatigue in human test drivers increases.

SUMMARY

One aspect of the disclosure provides a method of training a model for estimating likelihood of fatigue in test drivers. The method includes identifying training data including videos of the test drivers while such test drivers are tasked with monitoring driving of a vehicle operating in an autonomous driving mode, wherein the training data also includes driver drowsiness values generated from one or more human operators observing the videos; and using the training data to train the model such that when a new video of a first test driver is input into the model, the model will output an estimate of a likelihood of fatigue for the first test driver.

In one example, the training data further includes data corresponding to options selected by the one or more human operators observing the videos, wherein the options identify behaviors of test drivers related to fatigue. In this example, the options further identify whether test drivers are observing policies related to distractedness of test drivers. In this example, the policies include at least one policy relating to using a cell phone. In addition or alternatively, the policies include at least one policy relating to keeping hands on a steering wheel.

In another example, the training data further includes any fatigue events associated with the videos, and a fatigue event corresponds to a given test driver becoming distracted, closing his or her eyes for more than a predetermined period, or falling asleep. In this example, the training further enables the model to output a likelihood of the first test driver experiencing a future fatigue event.

In another example, the method also includes receiving user input corresponding to an abstract position on a sliding scale of driver drowsiness assessments; and converting the user input to one of the driver drowsiness values, wherein the one of the driver drowsiness values is a numerical value. In another example, each driver drowsiness value is associated with a reliability score, and wherein the model is further trained in order to provide a reliability score for the estimated likelihood of fatigue for the first test driver. In another example, the training data further includes intervention responses associated with the videos, each intervention response corresponding to an action to be taken in order to prevent a fatigue event corresponding to a given test driver becoming distracted, closing his or her eyes for more than a predetermined period, or falling asleep, and the model is further trained to provide a recommended intervention response for the first test driver.

Another aspect of the disclosure provides a system for estimating likelihood of fatigue in test drivers. The system includes one or more processors configured to: receive a video of a first test driver tasked with monitoring driving of a vehicle operating in an autonomous driving mode; input the video into a model in order to identify an estimated a likelihood of fatigue for the first test driver; and send the video to be reviewed by one or more human operators based on the likelihood of fatigue for the first test driver.

In one example, the one or more processors are further configured to: use the model to determine a reliability score for the estimated likelihood of fatigue; and determine a number of human operators for cross-validating the model, wherein the video is sent for review based on the determined number of human operators. In this example, the determining the number of human operators for cross-validating the model is further based on reliability scores associated with currently available human operators. In this example, the one or more processors are also configured to determine the reliability scores associated with the currently available human operators based on cross-validations by other human operators of videos observed by the currently available human operators.

In another example, the model further identifies an intervention recommendation for preventing a fatigue event in the first test driver, and wherein the video is sent to be reviewed based on the intervention recommendation, wherein the fatigue event corresponds to a given test driver becoming distracted, closing his or her eyes for more than a predetermined period, or falling asleep. In another example, the model further identifies a likelihood of the first test driver experiencing a future fatigue event, wherein a future fatigue event corresponds to a given test driver becoming distracted, closing his or her eyes for more than a predetermined period, or falling asleep. In another example, the one or more processors are further configured to input historical information related to fatigue events or interventions to prevent fatigue events for the first test driver into the model in order to estimate the estimated likelihood of fatigue for that test driver. In another example, the one or more processors are further configured to: use estimated likelihoods of fatigue for a plurality of test drivers to determine an average estimated likelihood of fatigue across the plurality of test drivers for a fleet of autonomous vehicles; and compare the average estimated likelihood of fatigue to a maximum allowable fatigue threshold. In this example, the one or more processors are further configured to use the comparison to identify test drivers to be removed from the test drivers for the fleet of vehicles. In another example, the model is a machine-learned model.

BRIEF DESCRIPTION OF THE DRAWINGS

FIG. 6 is an example user interface in accordance with aspects of the disclosure.

DETAILED DESCRIPTION

Overview

Figure 1:
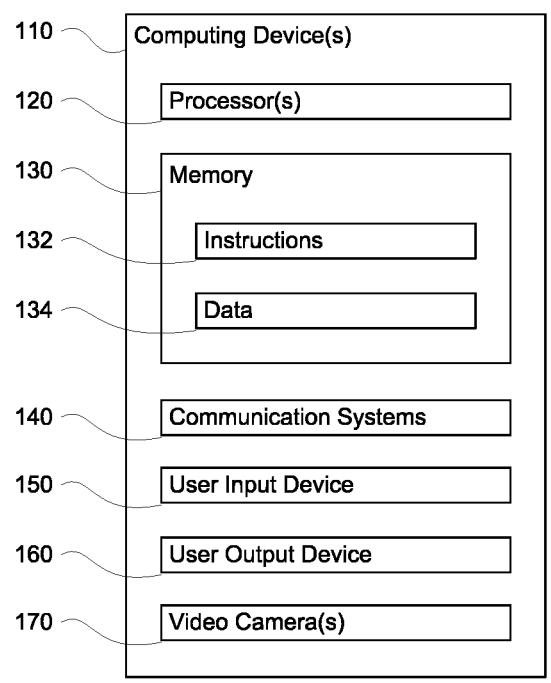
FIG. 1 is an example of a driver fatigue monitoring system.

The technology relates to preventing fatigue events in persons who are tasked with monitoring the driving of a vehicle operating in an autonomous driving mode. For instance, a person may be expected to monitor the vehicle and the vehicle's environment while the vehicle operates in the autonomous driving mode and be ready to immediately take control of the vehicle should the vehicle not be responding appropriately. Fatigue can result in fatigue events where a person becomes inattentive, closes his or her eyes, or even falls asleep. As such, it is critically important to ensure that autonomous vehicle operators remain attentive and are capable of continuing such monitoring and to intervene if needed.

As an initial step, these persons (hereafter, test drivers) may be monitored via one or more video cameras. The video cameras may be mounted overhead and/or in front of the test driver within the vehicle in order to best monitor the condition of the test or safety driver. For instance, every so often video of a test driver may be captured and sent to a remote server computing device. How often the video is captured and sent may be related to a number of human operators available to review the video (i.e. can be somewhat random), past performance of individual test drivers (e.g. test drivers who, where the test driver is with respect to his or her shift (more in the early and late stages of a shift and less in the middle), the number of test drivers within a vehicle, whether the test driver has met some certification requirement or some number of hours without a fatigue event, etc.

The video can then be monitored in real time (e.g. live streaming) or at a later time. A human operator may review the video and identify how that driver appears to be functioning. In this regard, the video may be at least some length, such as 30 seconds to 1 minute, in order to enable the human operator to make a reasonable assessment of the test driver. This may involve identifying a "driver drowsiness" value as well as other behaviors of the test driver which may relate to fatigue including whether his or her eyes are closed, whether he or she has yawned, etc. In addition, various radio buttons may enable the human operator to identify any observed behaviors related to drowsiness.

In some instances, a plurality of human operators may review the same video. In this regard, the driver drowsiness value and radio buttons single video may be "cross-validated" by the observations of additional human operators. In some instances, based on which radio buttons were selected for a given video, each test driver drowsiness value may be assigned a reliability score. The reliability of human operators may also be determined based on various factors. The selection or time allocation of human operators who should evaluate certain videos of particular test drivers may even be optimized using the reliability scores. In some instances, if the test driver drowsiness value is greater than a threshold, an intervention may be initiated. Various different types of intervention responses may be employed.

The videos, radio buttons and any intervention or fatigue even information may be used to train a model. For instance, for a given test driver, the model may provide an estimate of the likelihood of the driver being fatigued and/or experiencing a fatigue event at any given time. In some instances, the model may provide a recommended intervention that is appropriate for the estimated likelihood(s) and behaviors of the test driver exhibited during the video. In this regard, the model may be a machine learned model trained on various types of training inputs and training outputs.

The model itself may then be used in real time in order to monitor test drivers in real time and make recommendations. For instance, the streaming videos may be input into the model, which in turn, may output the aforementioned values and recommendations. In this regard, the model may be stored at a remote server computing device in order to reduce the amount of computing resources required at the vehicle. The precision and usefulness of these values may be improved as more of the aforementioned data is used to train the model. Of course, in a system that seeks to intervene before fatigue events in order to improve overall safety of the vehicles, higher recall may be preferred.

In other examples, self-reported fatigue values may be used to generate similar models which can also be used to monitor test drivers in real time and make recommendations.

The features described herein may provide for a reliable and effective system for identifying possible fatigue events in persons tasked with monitoring the driving of a vehicle operating in an autonomous driving mode. In other words, the model may enable the prediction and prevention of fatigue events prior to their occurrence. For instance, new test drivers or those who have yet to be hired may be "tested" using the model to predict how well that potential test driver is likely to perform if hired. In this regard, the model may ultimately help to manage fatigue risk by identifying test drivers who are likely to perform with the fewest fatigue events. In some instances, the model may also be used to inform how new test drivers should initially be monitored (e.g. the rate). As such, the model may also assist in assigning test drivers to the right task at the right time to reduce the likelihood of fatigue events across a fleet of vehicles and allocating resources more efficiently by balancing automated driver monitoring with human operator driver monitoring.

Example Systems

A driver fatigue monitoring system may include one or more computing devices 110 having one or more processors 120 and memory 130 storing instructions 132 and data 134. The memory 130 stores information accessible by the one or more processors 120, including instructions 132 and data 134 that may be executed or otherwise used by the processor 120. The memory 130 may be of any type capable of storing information accessible by the processor, including a computing device-readable medium, or other medium that stores data that may be read with the aid of an electronic device, such as a hard-drive, memory card, ROM, RAM, DVD or other optical disks, as well as other write-capable and read-only memories. Systems and methods may include different combinations of the foregoing, whereby different portions of the instructions and data are stored on different types of media.

The instructions 132 may be any set of instructions to be executed directly (such as machine code) or indirectly (such as scripts) by the processor. For example, the instructions may be stored as computing device code on the computing device-readable medium. In that regard, the terms "instructions" and "programs" may be used interchangeably herein. The instructions may be stored in object code format for direct processing by the processor, or in any other computing device language including scripts or collections of independent source code modules that are interpreted on demand or compiled in advance. Functions, methods and routines of the instructions are explained in more detail below.

The data 134 may be retrieved, stored or modified by processor 120 in accordance with the instructions 132. For instance, although the claimed subject matter is not limited by any particular data structure, the data may be stored in computing device registers, in a relational database as a table having a plurality of different fields and records, XML documents or flat files. The data may also be formatted in any computing device-readable format.

The one or more processor 120 may be any conventional processors, such as commercially available CPUs or GPUs. Alternatively, the one or more processors may be a dedicated device such as an ASIC or other hardware-based processor. Although FIG. 1 functionally illustrates the processor, memory, and other elements of computing device 110 as being within the same block, it will be understood by those of ordinary skill in the art that the processor, computing device, or memory may actually include multiple processors, computing devices, or memories that may or may not be stored within the same physical housing. For example, memory may be a hard drive or other storage media located in a housing different from that of computing device 110. Accordingly, references to a processor or computing device will be understood to include references to a collection of processors or computing devices or memories that may or may not operate in parallel.

The computing device 110 may include one or more video cameras 170 which may be configured to capture video and/or still images of a test driver. The computing device 110 may also include an output device 160, such as a display and/or speaker, as well as a user input device 150, such as a touchscreen, button(s), microphones, etc. in order to enable a test driver to input information into the computing device 110 and/or communicate with a remote operator. Such features may be used to enable a remote operator to "check-in" on a test driver as well as to enable two-way communications between the remote operator and the test driver. In some instances, the output device and the user input device may be the same device (e.g. a touchscreen).

The driver fatigue monitoring system 100 may also include a communications system 140 that enables the driver fatigue monitoring system 100 to communicate with other computing devices. For example, the communication system may include wired and/or wireless connections (such as transmitters and receivers), that enable the driver fatigue monitoring system to communicate with other computing devices. As an example, the communications system may enable the driver fatigue monitoring system to use various protocols including short range communication protocols such as Bluetooth, Bluetooth LE, the Internet, World Wide Web, intranets, virtual private networks, wide area networks, local networks, private networks using communication protocols proprietary to one or more companies, Ethernet, WiFi and HTTP, and various combinations of the foregoing. Such communication may be facilitated by any device capable of transmitting data to and from other computing devices, such as modems and wireless interfaces.

Figure 2:
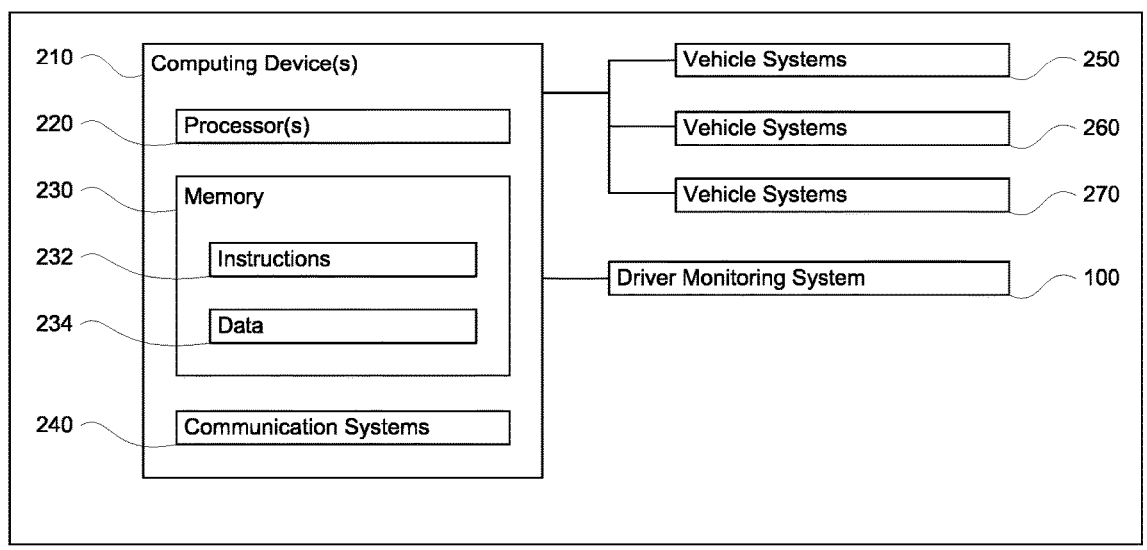
FIG. 2 is a functional diagram of an example vehicle in accordance with an exemplary embodiment.
Figure 3:
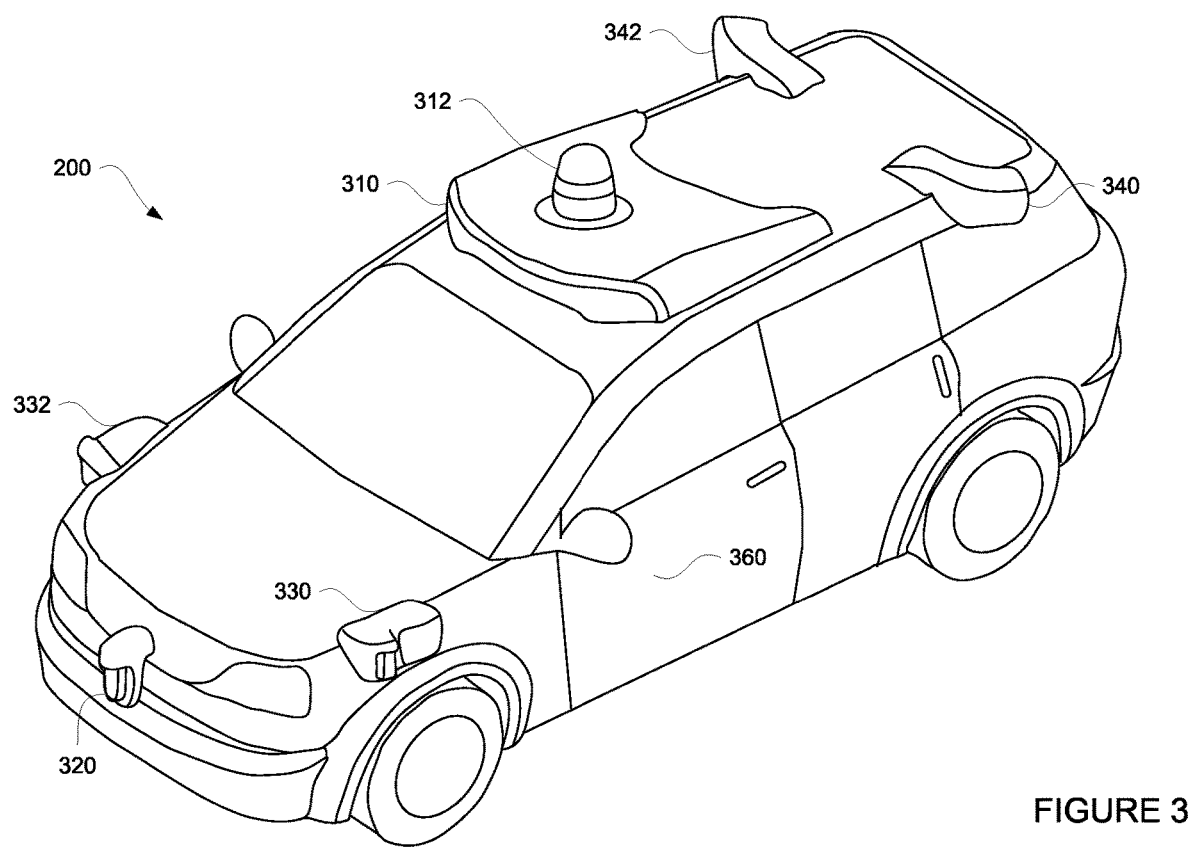
FIG. 3 is an example external view of a vehicle in accordance with aspects of the disclosure.

As noted above, the driver fatigue monitoring system may be employed within a vehicle having an autonomous driving mode. FIG. 2 is an example block diagram of a vehicle 200, and FIG. 3 is an example view of the vehicle 200. In this example, the vehicle 200 is a vehicle having an autonomous driving mode as well as one or more additional driving modes, such as a semiautonomous or manual driving mode. While certain aspects of the disclosure are particularly useful in connection with specific types of vehicles, the vehicle may be any type of vehicle including, but not limited to, cars, trucks, motorcycles, buses, recreational vehicles, etc.

Turning to FIG. 2, the computing devices 110 of the driver fatigue monitoring system may be in communication with one or more computing devices 210 of the vehicle. As shown, the driver fatigue monitoring system may be incorporated into the vehicle 200 and may also be incorporated into the computing devices 210.

The one or more computing devices 210 may include one or more processors 220, memory 230 storing instructions 232 and data 234, and other components typically present in general purpose computing devices. These processors, memory, instructions and data may be configured the same or similarly to the processors 120, memory 130, instructions 132, and data 134.

In one aspect the computing devices 210 may be part of an autonomous control system capable of communicating with various components of the vehicle in order to control the vehicle in an autonomous driving mode. For example, returning to FIG. 1, the computing devices 210 may be in communication with various systems 250, 260, 270 via wired or wireless connections. As an example, these systems may correspond to a deceleration system, an acceleration system, a steering system, a routing system for determining a route for the vehicle to follow between two or more locations, and planning system for planning a trajectory, a positioning system, a perception system for detecting objects in the vehicle's environment, etc. which the computing devices can use to control the vehicle 200 in the autonomous and semi-autonomous driving modes.

Turning to FIG. 3, as an example, the vehicle 200 includes a roof-top housing 310 and dome housing 312 may include a LIDAR sensor as well as various cameras and radar units. In addition, housing 320 located at the front end of vehicle 200 and housings 330, 332 on the driver's and passenger's sides of the vehicle may each store a LIDAR sensor. For example, housing 330 is located in front of driver door 360. Vehicle 200 also includes housings 340, 342 for radar units and/or cameras also located on the roof of vehicle 200. Additional radar units and cameras (not shown) may be located at the front and rear ends of vehicle 200 and/or on other positions along the roof or roof-top housing 310.

The computing devices 210 may include a communications system 240 which may be the same or similar to communications system 140. The communications system may enable the computing devices 210 to communicate with other devices remote from the vehicle. In this way, information from the driver fatigue monitoring system 100 may be sent to remote devices. As such, the driver fatigue monitoring system may 100 be able to communicate with the computing devices 210 of the vehicle as well as various remote computing devices, such as those computing devices that are a part of the autonomous vehicle service as well as other computing devices, either directly or indirectly via the computing devices of the vehicle.

Figure 4:
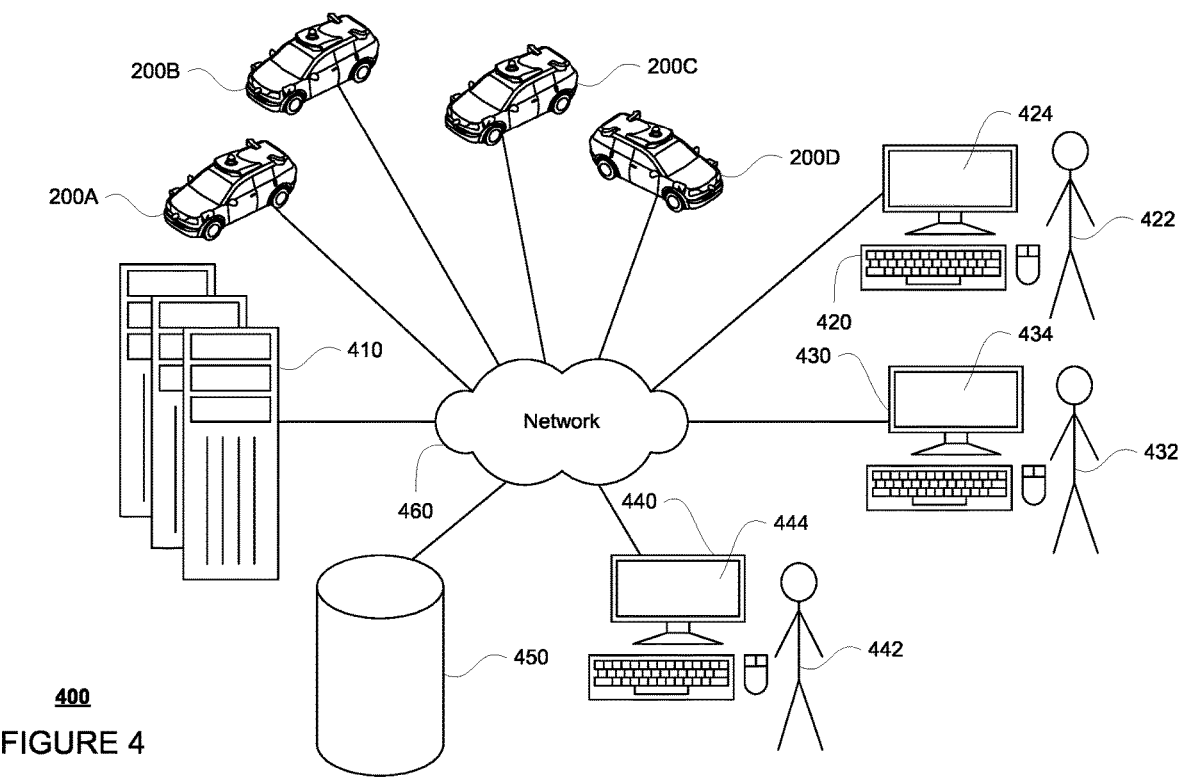
FIG. 4 is an example pictorial diagram of a system in accordance with aspects of the disclosure.
Figure 5:
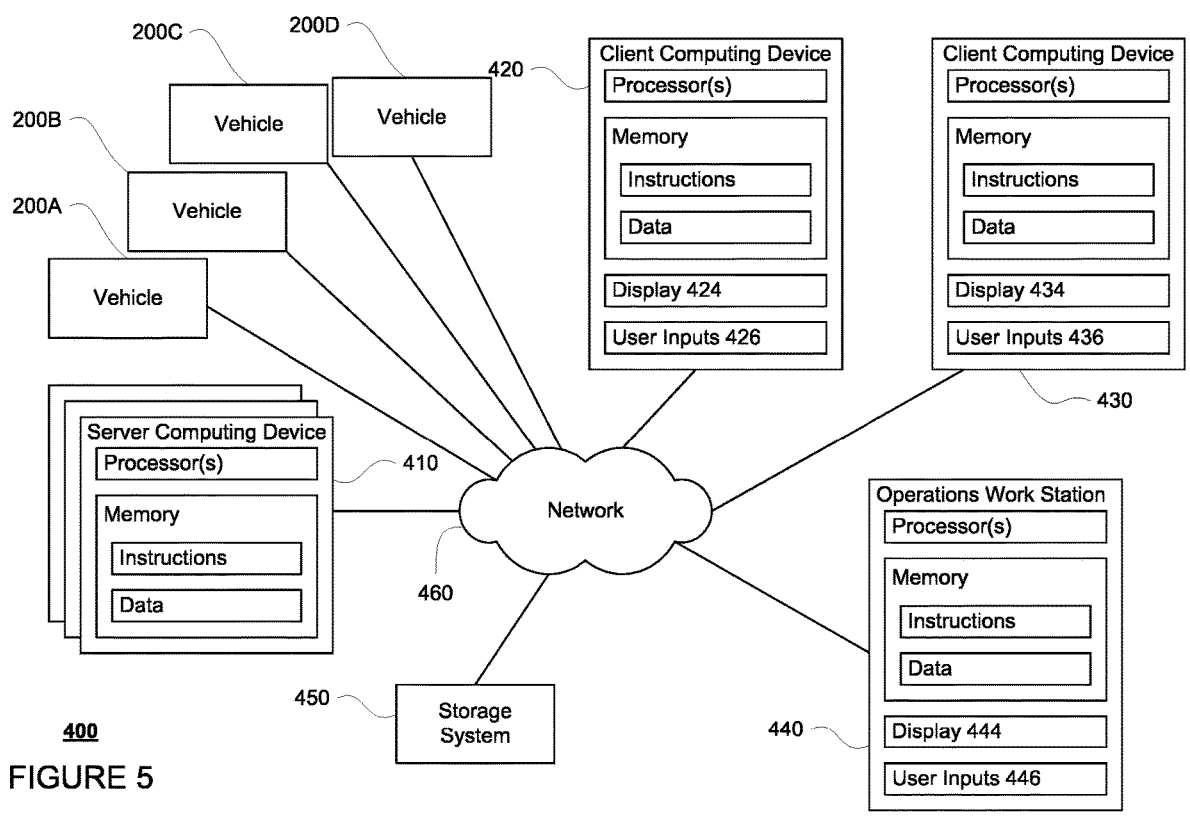
FIG. 5 is an example block diagram of the system of FIG. 4.

FIGS. 4 and 5 are pictorial and functional diagrams, respectively, of an example system 400 that includes a plurality of computing devices 410, 420, 430, 440 and a storage system 450 connected via a network 460. System 400 also includes vehicles 200A, 200B, 200C, 200D, which may be configured the same as or similarly to vehicle 200. Although only a few vehicles and computing devices are depicted for simplicity, a typical system may include significantly more.

As shown in FIG. 4, each of computing devices 410, 420, 430, 440 may include one or more processors, memory, data and instructions. Such processors, memories, data and instructions may be configured similarly to one or more processors 120, memory 130, data 134, and instructions 132 of computing device 110.

The network 460, and intervening nodes, may include various configurations and protocols including short range communication protocols such as Bluetooth, Bluetooth LE, the Internet, World Wide Web, intranets, virtual private networks, wide area networks, local networks, private networks using communication protocols proprietary to one or more companies, Ethernet, WiFi and HTTP, and various combinations of the foregoing. Again, communication may be facilitated by any device capable of transmitting data to and from other computing devices, such as modems and wireless interfaces.

In one example, one or more computing devices 410 may include one or more server computing devices having a plurality of computing devices, e.g., a load balanced server farm, that exchange information with different nodes of a network for the purpose of receiving, processing and transmitting the data to and from other computing devices. For instance, one or more computing devices 410 may include one or more server computing devices that are capable of communicating with computing device 210 of vehicle 200 or a similar computing device of other vehicles as well as computing devices 420, 430, 440 via the network 460. For example, each of the vehicles 200A, 200B, 200C, 200D, may correspond to vehicle 200 and may be a part of a fleet of vehicles of the autonomous vehicle service that can be dispatched by server computing devices 410 to various locations. In this regard, the server computing devices 410 may function (in conjunction with storage system 450) as a dispatching system for the autonomous vehicle service which can be used to dispatch vehicles such as vehicle 200 and vehicle 200A to different locations in order to pick up and drop off passengers. In addition, server computing devices 410 may use network 460 to transmit and present information to a person, such as human operators 422, 432, 442 on a display, such as displays 424, 434, 444 of computing devices 420, 430, 440. In this regard, computing devices 420, 430, 440 may be considered client computing devices.

As shown in FIG. 4, each client computing device 420, 430, 440 may be a personal computing device intended for use by a human operator 422, 432, 442, and have all of the components normally used in connection with a personal computing device including a one or more processors (e.g., a central processing unit (CPU)), memory (e.g., RAM and internal hard drives) storing data and instructions, a display such as displays 424, 434, 444 (e.g., a monitor having a screen, a touch-screen, a projector, a television, or other device that is operable to display information), and user input devices 426, 436, 446 (e.g., a mouse, keyboard, touchscreen or microphone). The client computing devices may also include a camera for recording video streams, speakers, a network interface device, and all of the components used for connecting these elements to one another.

Although the client computing devices 420, 430, and 440 may each comprise a full-sized personal computing device, they may alternatively comprise mobile computing devices capable of wirelessly exchanging data with a server over a network such as the Internet. By way of example only, the client computing devices may include a mobile phone or a device such as a wireless-enabled PDA, a tablet PC, a wearable computing device or system, or a netbook that is capable of obtaining information via the Internet or other networks.

Each of the client computing devices may be remote monitoring workstation used by a person (e.g. human operators 422, 432, 442) to provide concierge or remote assistance services to test drivers of vehicles 200A, 200B, 200C, 200D. For example, a human operator 442 may use the remote monitoring workstation 440 to communicate via a telephone call or audio connection with people through their respective client computing devices or vehicles 200A, 200B, 200C, 200D, in order to ensure the safe operation of vehicles 100 and 100A and the safety of the test drivers as described in further detail below. Although only a few remote monitoring workstations are shown in FIGS. 4 and 5, any number of such work stations may be included in a typical system.

As with memory 130, storage system 450 can be of any type of computerized storage capable of storing information accessible by the server computing devices 410, such as a hard-drive, memory card, ROM, RAM, DVD, CD-ROM, write-capable, and read-only memories. In addition, storage system 450 may include a distributed storage system where data is stored on a plurality of different storage devices which may be physically located at the same or different geographic locations. Storage system 450 may be connected to the computing devices via the network 460 as shown in FIGS. 3 and 4, and/or may be directly connected to or incorporated into any of the computing devices 410, 420, 430, 440, etc.

The storage system 450 may be configured to store various information including videos, driver drowsiness values, radio button selections, thresholds, test driver information, human operator information, reliability scores for human operators, intervention or fatigue event information, models, model data (e.g. parameters), etc. as discussed further below.

Example Methods

In addition to the operations described above and illustrated in the figures, various operations will now be described. It should be understood that the following operations do not have to be performed in the precise order described below. Rather, various steps can be handled in a different order or simultaneously, and steps may also be added or omitted.

As noted above, a test driver may be able to self-report fatigue using a user input of the vehicle. For instance, a test driver may utilize user input devices of vehicle 200A to input information about how the driver is doing or may use an application installed or a web browser interface of the test driver's client computing device (e.g. cell phone). As an example, a test driver may report fatigue using a periodic fatigue scale (PFS) such as the Karolinska Sleepiness Scale (KSS) or other modified scales. In this regard, a test driver may input a value on some scale to indicate a level of alertness, fatigue, and/or sleepiness. This value may then be sent by the computing devices 110 and/or the test driver's client computing device to the server computing devices 410 for further processing and/or storage in the storage system 450.

In this regard, prior to starting a new shift monitoring an autonomous vehicle, a test driver may self-report their level of alertness, fatigue, and/or sleepiness using the PFS. Thereafter, the test driver may self-report the current level of alertness, fatigue, and/or sleepiness using the PFS periodically, such as once every two hours of monitoring (inclusive or exclusive of breaks), or more or less often. In some instances, for any breaks, the test driver may be asked or required to report their level of alertness, fatigue, and/or sleepiness using the PFS prior to resuming monitoring. As indicated above, these PFS values may be sent to the server computing devices 410 and stored in the storage system 450.

The server computing devices 410 may also use the values to trigger an alert system and/or a set of procedures to avoid a fatigue event. For example, if the PFS is a 9-point scale, where PFS values of 6 or more are considered to constitute fatigue, a test driver who reports a PFS value of 6 or more will cause the server computing devices 410 to send an alert to an operator such as a dispatcher who can provide assistance such as by asking whether the driver needs a ride back to base or suggesting they attempt a countermeasure, such as mild exercise to reduce fatigue. In this regard, PFS values of 6 or more may be considered to be self-reported fatigue events which may be stored in the storage system 450 as noted above.

As noted above, the technology relates to preventing fatigue events in persons who are tasked with monitoring the driving of a vehicle operating in an autonomous driving mode, such as vehicles 200A, 200B, 200C, 200D. For instance, one of human operators 422, 432, 442 may be expected to monitor the vehicle 200A and the vehicle's environment while the vehicle operates in the autonomous driving mode.

For instance, a person may be expected to monitor the vehicle and the vehicle's environment while the vehicle operates in the autonomous driving mode and be ready to immediately take control of the vehicle should the vehicle not be responding appropriately. Fatigue can result in fatigue events where a person becomes inattentive, closes his or her eyes, or even falls asleep. As such, it is critically important to ensure that autonomous vehicle operators remain attentive and are capable of continuing such monitoring and to intervene if needed.

Figure 6:
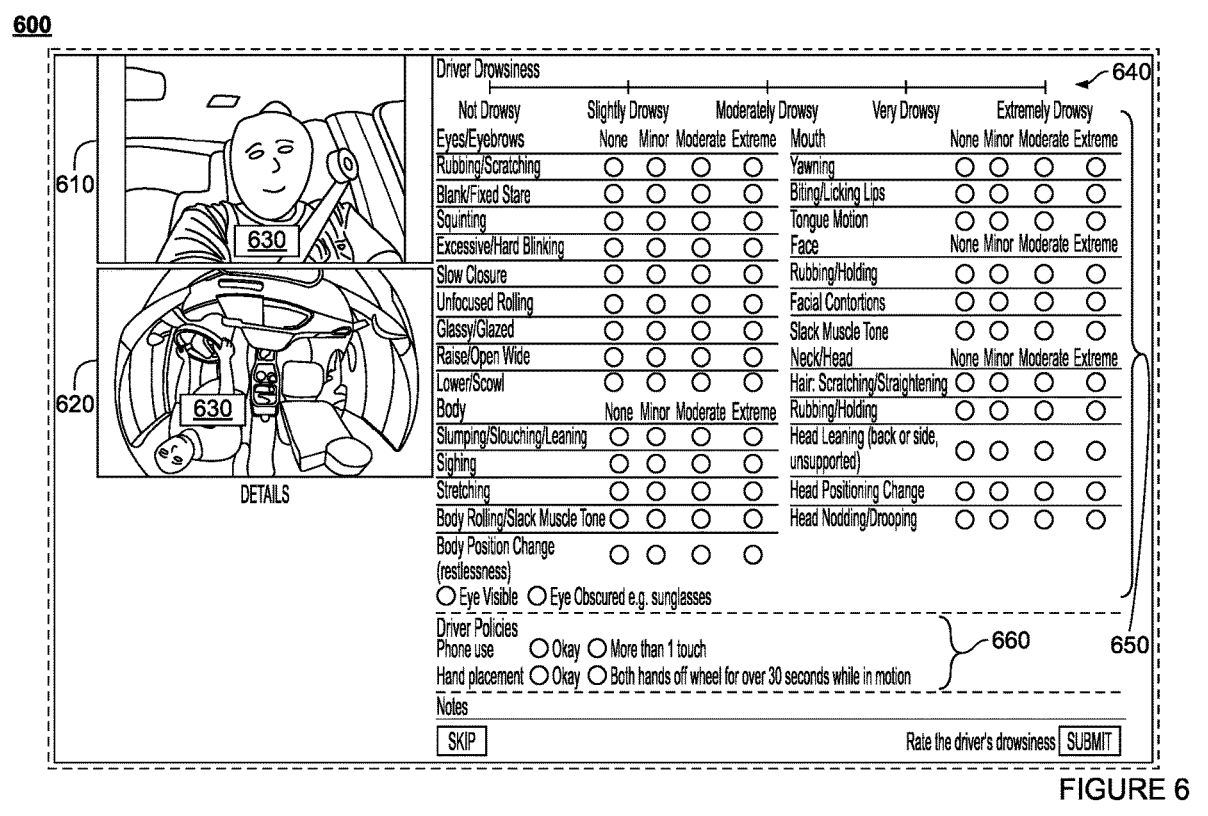

As an initial step, these persons tasked with monitoring vehicles driving in an autonomous driving mode may be monitored via the one or more video cameras 170. The video cameras may be mounted overhead and/or in front of the test driver within the vehicle in order to best monitor the condition of the test or safety driver. For example, FIG. 6, depicts a pair of videos 610, 620 (or rather, video feeds) from the one or more video cameras 170 of any of vehicles 200A, 200B, 200C, 200D. Video 610 may be from a camera mounted at a headliner of a vehicle and/or proximate to a rear-view mirror of the vehicle and oriented towards test driver 630. Video 620 may be from a camera mounted at a headliner above and oriented downwards towards the test driver 630

Every so often video of a test driver may be captured by a driver fatigue monitoring system, such as the driver fatigue monitoring system 100, and sent to a remote server computing device, such as server computing devices 410. Such videos may also be stored, for instance, in the storage system 450. How often the video is captured and sent may be related to a number of human operators available to review the video (i.e. can be somewhat random), past performance of individual test drivers (e.g. test drivers who, where the test driver is with respect to his or her shift (more in the early and late stages of a shift and less in the middle), the number of test drivers within a vehicle, whether the test driver has met some certification requirement or some number of hours without a fatigue event, etc. The videos of test drivers can then be monitored in real time (e.g. live streaming) or at a later time.

A human operator may review the video and identify how that test driver appears to be functioning. In this regard, the video may be streamed continuously "live" or be at least some length, such as 30 seconds to 1 minute, captured immediately prior to being viewed. In some instances, the remote operator may be required to view the video for at least some period of time, such as 30 seconds or more or less, in order to enable the human operator to make a reasonable assessment of the test driver. This may involve identifying a "driver drowsiness" value as well as other behaviors of the test driver which may relate to fatigue including whether his or her eyes are closed, whether he or she has yawned, etc. In this regard, FIG. 6 represents an example user interface 600 that can be displayed on any of displays 424, 434, 444 to a human operator. In this example, the driver drowsiness value may appear as an abstract value which the human operator selects on a sliding scale 640. The position on the scale may be translated to a fixed range of numerical values (e.g. from 0 to 100, where 0 is wide awake or not drowsy and 100 is extremely drowsy). In this regard, each abstract position on the scale may correspond to (e.g. be converted to) a numerical value.

In addition, various radio buttons 650 may enable the human operator to identify any observed behaviors related to drowsiness. In some instances, the radio buttons may relate to a test driver's eyes or eyebrows and may include, for example, rubbing or scratching eyes or eyebrows, a blank or fixed stare, squinting, excessive or hard blinking, slow closure of eyes, unfocused eye rolling, glassy or glazed eyes, raised eyebrows or eyes that are open wide, lowered eyebrows or a scowl, etc. Some radio buttons may relate to the test driver's body and may include, for example, slumping, slouching or leaning, signing, stretching, body rolling or slack muscle tone, body position change that may indicate restlessness, etc. Radio buttons may also relate to the test driver's mouth and may include, for example, yawning, biting or licking lips, tongue motion, etc. Other radio buttons may relate to the test driver's overall face, for example, rubbing or holding, facial contortions, slack muscle tone, etc. Radio buttons may also relate to the test driver's neck or head, for example, hair scratching or straightening, rubbing or holding the head or next, head leading to the back or side or unsupported, head positioning change, head nodding or drooping, etc. to Still other radio buttons 660 may enable the human operator to confirm whether the test driver is observing various policies related more to distractedness (rather than to fatigue), such as using a cell phone or keeping his or her hands on the steering wheel.

In some instances, the specific radio buttons selected may be used to adjust the scale value. For instance, when a radio button for slow eye closure is selected, this may result in blocking the lower end of the scale, such that only the position on the scale corresponding to values 50-100 can be selected, but not the values 0-49.

In addition or alternatively, combinations of radio buttons may be correlated with driver drowsiness values. For example, in cases where the driver drowsiness value provided by a human operator who has selected a particular radio button combination is at or below two standard deviations from the average driver drowsiness value associated with that radio button combination, the driver drowsiness value may be adjusted toward the average driver drowsiness value, or the system may respond as if the human had rated the value as the average value. Similarly, in cases of disagreement between the human operator identified driver drowsiness values and radio-button average driver drowsiness value, the system may respond to the more conservative of the two values (i.e., whichever approach predicts the high fatigue level).

In some instances, specific radio buttons could also trigger immediate changes in video sampling frequency. For example, eye closure (of radio buttons 660) may justify more frequent monitoring but it's absence could justify less frequent monitoring.

The selected radio buttons, drowsiness values, and videos may be associated with one another and stored for later use, for example, in storage system 450.

In some instances, a plurality of human operators may review the same video. In this regard, the driver drowsiness value and radio buttons single video may be "cross-validated" by the observations of 2 or more additional human operators. For example, two or more of human operators 422, 432, 442 may each review the videos 610, 620 and input a driver drowsiness value using the sliding scale 640 as well as select various of the radio buttons 650, 660. In such instances, one or more of the highest driver drowsiness values, an average driver drowsiness value, or all of the driver drowsiness values may be associated with the video. Similarly, the radio button responses associated with each video may include all such information input by the human observers, or only those which were selected by some minimum number of human observers, such as two or more. This may improve the reliability of the driver drowsiness values which are subjective and thus, eliminate or account for outlier observations.

In some instances, based on which radio buttons were selected for a given video, each driver drowsiness value may be assigned a reliability score by one or more server computing devices such as the server computing devices 410. For example, if eye closure was assessed (via the use of the radio button), an initial rating that correlates well with the cross-validated ratings may be assigned a higher reliability score, which could mean that fewer additional human operators would be needed to cross validate. This, in turn, can be used to determine reliability scores for human operators. In this regard, those human operators who tend to be more consistent with and typically require fewer additional human operators for cross validation would have higher reliability scores. In addition, the number of human operators required for validation may be adjusted based upon the reliability scores of currently available human operators (e.g. those available to review videos). For example, cross-validating may require only 3 human operators with higher reliability scores or five human operators with lower reliability scores. In some instances, driver drowsiness values provided by human operators can also be weighted by the reliability of those human operators, such that more reliable human operators have more influence over the resulting average than less reliable human operators.

The reliability of human operators may also be determined by one or more server computing devices, such as the server computing devices 410, based on various factors. For instance, a reliability score for a human operator may be determined based on the radio buttons selected as compared to those selected by other human operators watching the same video or rather, how well the human operator agrees with other raters. For example, 3 out of 4 human operators selected the moderate yawning radio button of the radio buttons 650, and one did not, this may indicate that the reliability score of the one human operator should be lower for this rating, e.g. it is an outlier rating. Such determinations could be made on the basis of statistics or more complex machine learning models. In addition or alternatively, reliability scores may be based on the human operator's evaluations of a predefined set of videos for calibration. In addition or alternatively, the reliability score of a human operator may be based on their performance over time. For example, some human operators' reliability may degrade over time (e.g. later in their shift), such that fresh operators are more reliable. The reliability score of a human operator may also be based on their total performance history or a rolling window of a week, 2 weeks, etc. In some instances, human operators who provide several sequential outlier ratings as being temporarily of low reliability, even if their performance history otherwise suggests they are highly reliable. Other factors that may affect reliability scores may include the difficulty to rate a given test driver which may be defined as variance of scores given to a given test driver across all fatigue events and human operators as some test drivers may be harder to evaluate as evidenced by variance in driver drowsiness values.

In some instances, human operators may be selected by one or more server computing devices such as the server computing devices 410 to review particular videos or drivers. This selection or time allocation of human operators who should evaluate certain videos of particular test drivers may even be optimized using the reliability scores. For instance, human operators, such as human operators 422, 432, 442 may be selected based on how difficult it has been in the past to evaluate a particular test driver or how likely the test driver is to have a fatigue event or a fatigue event at a particular date/time based on the test driver's past history. In such cases, more highly reliable (e.g. those with higher reliability scores) may be selected to review such videos. In addition, human operators may be assigned to either an initial review of a video or a cross validation of a driver drowsiness values based on reliability scores. In this regard, human operators with lower reliability scores may monitor live videos as a first signal, and human operators with higher reliability scores may do cross validation.

In some instances, if the driver drowsiness value (any value, highest value, or an average value as described above) is greater than a hand-tuned or algorithmically generated (based on the relationship between fatigue and operator performance) threshold, such as greater than moderately drowsy or an arbitrary value such as "67" or greater, an intervention may be initiated by one or more server computing devices such as the server computing devices 410. Various different types of intervention responses may be employed. For instance, intervention responses may include providing the test driver with supportive options and, if applicable, task-reassignment. For example, the test driver may be provided with a set of tasks to get the test driver more engaged or further evaluate fatigue, connected with a remote assistance operator who can interact with the person, or even relieved of the duty of monitoring a vehicle for a current shift. If any interventions are made for a particular test driver, a fatigue event is identified by software (such as software commonly used to determine if a person's eyes are closed in a video for longer than a predetermined period of time), or a fatigue event occurs and is reported by a test driver (e.g. based on the PFS values) or a human operator, these can be associated with any videos captured immediately before the intervention or fatigue event and stored for later user.

The videos, radio buttons and any intervention or fatigue event information may be used by one or more server computing devices, such as the server computing devices 410, in order to train a first model. For a given test driver, the first model may provide an estimate of the likelihood of a test driver being fatigued and/or experiencing a fatigue event at any given time. This may enable the human operators to directly or more frequently monitor those test drivers that have the highest likelihood of future fatigue events and thereby provide a better allocation of such resources.

In some instances, the first model may provide a recommended intervention that is appropriate for the estimated likelihood(s) and behaviors of the test driver exhibited during the video. Example recommendations may include flagging the video and/or the test driver for review by human operators (e.g. human operators may be used to cross-validate the model), stop the test driver (e.g. pull the vehicle over and/or end the shift of the test driver), initiate tests (e.g. alertness tests, reaction time tests, performance test, etc.), send a signal to remote assistance to check in of that test driver, open a window or lower air conditioning within the vehicle, require that the test driver take a break, require that the test driver drive the vehicle manually, take more turns, turn on music within the vehicle, a task for the test driver, etc. Tasks may include giving rides to passengers, collecting data for mapping, cruising without passengers, performing non driving work, etc.

Figure 7:
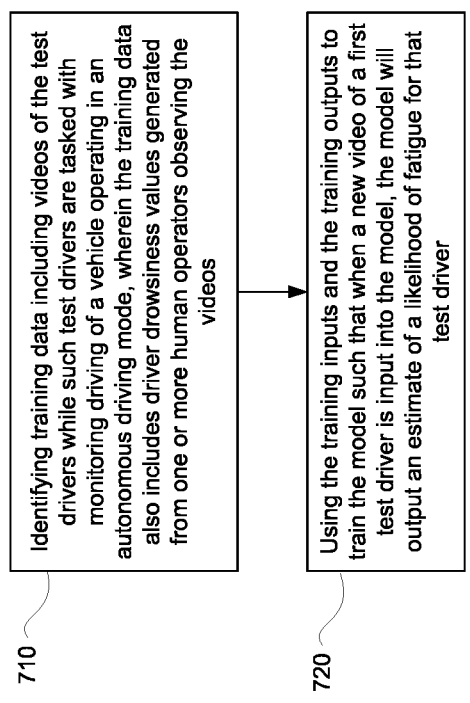
FIG. 7 is an example flow diagram in accordance with aspects of the disclosure.

FIG. 7 represents an example flow diagram 700 for training a model which may be performed by one or more processors of one or more server computing devices, such as the processors of server computing devices 410. At block 710, training data including videos of the test drivers while such test drivers are tasked with monitoring driving of a vehicle operating in an autonomous driving mode is identified. The training data also includes driver drowsiness values generated from one or more human operators observing the videos. At block 720, the training inputs and the training outputs may be used to train the model such that when a new video of a first test driver is input into the model, the model will output an estimate of a likelihood of fatigue for that test driver For instance, the first model may be machine-learned models trained on various types of training inputs and training outputs. For example, the training inputs for the first model may include the aforementioned videos of test drivers. The training outputs may include the radio buttons (associated with the aforementioned videos) and driver drowsiness values. The first model could "learn" that certain radio buttons better predict cross-validated fatigue scores and another computer vision model, could be trained to detect visual patterns indicative of fatigue or a specific radio button. In addition or alternatively, two models could be used, one based on understanding how predictive specific radio button values are of fatigue and another using computer vision to pre-populate radio buttons or provide an additional predictor of cross-validated fatigue.

In some instances, the videos may be processed to identify certain driver behaviors using known software to identify information such as eye movement, eye state (e.g. open or closed), head movement, gaze vector, whether the test driver is looking at an object outside of or inside of the vehicle, etc., though such information may not be necessary. Additional training inputs may include the current state of the test driver with respect to his or her shift (e.g. beginning 30 minutes, middle, ending 30 minutes, how close to a next break or last break, etc.).

The training outputs for the first model may include the driver drowsiness values and any interventions and/or fatigue events associated with the videos. In this regard, the first model may be trained to provide an estimated likelihood of fatigue which may correspond to a driver drowsiness value and an estimated likelihood of a fatigue event. As noted above, the training interventions may enable the first model to output a recommendation based on the predicted fatigue. In addition, the training outputs may also include the aforementioned reliability scores. In this regard, the model may output a reliability score for its assessment of each test driver. The first model and trained model parameter values may then be stored for later use, for instance, in storage system 450.

As an alternative to the radio buttons, the videos, PFS values, and any intervention or fatigue event information could be by one or more server computing devices, such as the server computing devices 410, in order to train a second model. For a given test driver, the second model may provide an estimate of the test driver's PFS value which may indicate the likelihood of a test driver being fatigued and/or experiencing a fatigue event at any given time. This may enable the human operators to directly or more frequently monitor those test drivers that have the highest likelihood of future fatigue events (e.g. higher PFS values) and thereby provide a better allocation of such resources. In addition, the model may be trained to provide a recommended intervention, such as those described above, for a test driver given the test driver's PFS value.

As with the example above, the second model may be machine-learned models trained on various types of training inputs and training outputs. The training inputs for the second model may include the aforementioned videos. The training outputs for the second model may include the PFS values and any interventions and/or fatigue events associated with the videos and/or PFS values. In this regard, the second model may be trained to provide an estimated likelihood of fatigue which may correspond to PFS value and an estimated likelihood of a fatigue event occurring. In some instances, if the PFS values for a particular test driver did not correlate well with the driver drowsiness values provided by a human operator, this may lower the weighing of the PFS values for that test driver or the PFS values may be discarded. As noted above, the training interventions may enable the second model to output a recommendation based on the estimated likelihood of fatigue. The second model and trained model parameter values may then be stored for later use, for instance, in storage system 450.

Figure 8:
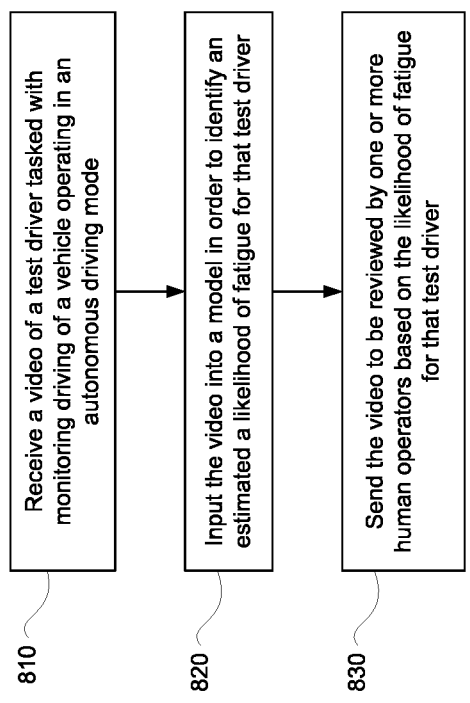
FIG. 8 an example flow diagram in accordance with aspects of the disclosure.

The first and/or the second models may then be used by one or more server computing devices, such as the server computing devices 410, in real time in order to monitor test drivers in real time and make recommendations. FIG. 8 represents an example flow diagram 800 for estimating the likelihood of fatigue in test drivers which may be performed by one or more processors of one or more server computing devices, such as the processors of server computing devices 410. In this example, video of a test driver tasked with monitoring driving of a vehicle operating in an autonomous driving mode is received at block 810. At block 820, the video is input into a model in order to identify an estimated likelihood of fatigue for that test driver. At block 830, the video may be sent to be reviewed by one or more human operators based on the likelihood of fatigue of that test driver.

For instance, the aforementioned videos may be input into one or both of the first and second models by one or more server computing devices such as the server computing devices 410. The first and second models, in turn, may output the aforementioned values and recommendations. In this regard, the first and second models may be stored at a remote server computing device in order to reduce the amount of computing resources required at the vehicle. The precision and usefulness of these values may be improved as more of the aforementioned data is used to train the model. Of course, in a system that seeks to intervene before fatigue events in order to improve overall safety of the vehicles, higher recall may be preferred.

In some instances, the recommendations may also be based on historical data for a particular test driver. In this regard, data about the mission such as number of breaks taken, duration of the breaks, time since last break, number for vehicle disengages, average speed, complexity of road situation etc. as well as rates of interventions, fatigue events, etc. and related information may also be input into the model each time a new video is processed. For example, a particular test driver may more reliably express fatigue with a sequence of yawns. In such cases, the first and/or the second model may ascribe to that test driver a predictive weight to yawns that is beyond that of a typical test driver. In other words, models may be trained using historical video and behavioral data to identify the unique leading indicator of fatigue for that specific individual. Also once a recommendation is given, the recommendation may be scored in terms of how well it worked in terms of the impact on driver drowsiness scores and post-intervention driving record. In this regard, the best performing recommendations can be selected in the future for this or even other test drivers.

As noted above, the first model may also output a reliability score. In the event that the first model recommends sending the video and/or additional videos of the test driver for review by human operators, the reliability score may be used to inform the number of human operators required to cross validate the model. In other words, for a lower reliability score, more human operators may be required to cross-validate or only human operators with higher reliability scores themselves. Other contributors of reliability may also be modeled: difficulty to rate a given test driver (as described above), time on shift/task, reliability within a rolling daily/weekly window, etc. Another way to account for differences in rater reliability is to assign a weight to their score in proportion to their reliability. By doing this, the average cross-validated value may be more influenced by more reliable raters.

The first and/or second models may also be used by one or more server computing devices, such as the server computing devices 410, to provide additional information or suggestions for a particular test driver. For instance, the output of the first and/or second models may be used to inform days of the week and shift hours which each particular test driver may be likely to perform best (e.g. be the least fatigued). In addition, the output of the first and/or second models may be used to determine a baseline monitoring rate for each test driver. One way to determine the baseline monitoring rate for a test driver is to use their prior fatigue history to determine the probability distribution of their medium or high fatigue events. A given test driver may be found to be extremely unlikely to experience fatigue at some intervals within the day but fairly likely to begin to experience fatigue in others. The baseline monitoring rate could be set in proportion to the fatigue probability.

In some instances, for days of the week or hour of the day variance the first and/or second model may include day of the week variable or hour of the day variable for the entire test driver population and on top of that an individual day of week or hour of the day variable individual to each test driver. As an example, for a group of 100 test drivers, there would be 101-day and 101-hour variables. This may be similar to a panel regression that has group and individual level variables.

In some instances, for baseline monitoring rate, an optimization problem may be solved by one or more server computing devices, such as the server computing devices 410, in order to maximize the recall of fatigue events while limiting the number of human operators required to monitor test drivers. This of course must be balanced against the limited amount of time available for human operators to monitor test drivers, a recall function, as well as historical values of average driver fatigue risk (e.g. higher risk test drivers should be monitored more frequently). The recall or frequency function may be upward sloped, meaning that recall is higher with higher frequency, but the return on increasing frequency may be declining as frequency goes up.

In addition, the first model may be used by one or more server computing devices, such as the server computing devices 410, to identify combinations of radio buttons are more likely to result in fatigue events and/or changes in those radio buttons over time (e.g. over different observations) that are more or less likely to lead to a fatigue event. In this regard, the first model may also identify which groups of test drivers exhibit similar behaviors before expected or past fatigue events. For example, the first model may identify those test drivers which typically rub their face prior to fatigue events. Such information may then be used to inform the estimated likelihoods provided by the model for particular test drivers (e.g. those within particular groups). For instance, regression of historical driver drowsiness values (dependent variable) could be determined based on metadata (radio buttons, independent variables) and used to understand which of the radio buttons are most predictive of fatigue events as well as the lag between radio button value signaling fatigue and actual fatigue being observed. In addition or alternatively, a subset of high fatigue events could be ranked according to the highest frequency metadata (radio buttons) such as if face rubbing is observed in most of fatigue events, more active action could be taken for observations with similar metadata values, such as frequently cross-validating videos where test drivers are rubbing their face.

The first and/or second models may also be used by one or more server computing devices, such as the server computing devices 410, to assess an overall likelihood of fatigue at any given moment across a plurality of test drivers for a fleet of vehicles. For example, management of the fleet of vehicles, such as vehicles 200A, 200B, 200C, 200D may require that the fleet stay within or below a maximum allowable fatigue threshold or expected likelihood of fatigue or a fatigue event across all test drivers (e.g. a maximum average value). If the actual average expected likelihood values determined from the models for each test driver currently working exceed this maximum allowable fatigue threshold, those test drivers with the highest expected likelihoods of fatigue and/or fatigue events may be removed (e.g. taken off shift or given a break) until the average (or averages) are below the maximum.

Observing fatigue at fleet level, such as identifying the total number of fatigue events per hour for the entire fleet, may allow for more proactive management of fatigue by impacting break schedules, break duration and changing frequency and types of interactive cognitive tasks. Additionally, this may impact driving areas assigned to a fleet or individual driver. For instance, at times of higher fatigue events, vehicles may be sent to areas with less intense traffic to minimize safety risk or assign a different portfolio of tasks. Similarly, if some tasks are more fatiguing, those tasks would be reduced and instead, less fatiguing tasks would be given or assigned. In addition or alternatively, upon some conditions the decision may be made to convert a fleet into dual test driver mode from single test driver mode (e.g. two test drivers rather than just one may be assigned to a single vehicle).

In addition, similar techniques may be used to monitor test drivers in a simulated environment. This data could be used to differentiate fatigue prone test drivers from those well suited for long duration autonomous supervision.

In addition, the approaches described herein may impact hiring decisions for new test drivers, incentive pay and task mix that test drivers can perform. For example, based on output of the first and/or second model the test driver may be assigned to a different driving area, maximum speed of the vehicle can be adjusted, different fatigue management tools can be used (break durations, number of breaks, number and types of interactive cognitive tasks), etc.

The features described herein may provide for a reliable and effective system for identifying possible fatigue events in persons tasked with monitoring with monitoring the driving of a vehicle operating in an autonomous driving mode. In other words, the model may enable the prediction and prevention of fatigue events prior to their occurrence. For instance, new test drivers or those who have yet to be hired may be "tested" using the model to predict how well that potential test driver is likely to perform if hired. In this regard, the model may ultimately help to manage fatigue risk by identifying test drivers who are likely to perform with the fewest fatigue events. In some instances, the model may also be used to inform how new test drivers should initially be monitored (e.g. the rate). As such, the model may also assist in assigning test drivers to the right task at the right time to reduce the likelihood of fatigue events across a fleet of vehicles and allocating resources more efficiently by balancing automated driver monitoring with human operator driver monitoring.

Unless otherwise stated, the foregoing alternative examples are not mutually exclusive, but may be implemented in various combinations to achieve unique advantages. As these and other variations and combinations of the features discussed above can be utilized without departing from the subject matter defined by the claims, the foregoing description of the embodiments should be taken by way of illustration rather than by way of limitation of the subject matter defined by the claims. In addition, the provision of the examples described herein, as well as clauses phrased as "such as," "including" and the like, should not be interpreted as limiting the subject matter of the claims to the specific examples; rather, the examples are intended to illustrate only one of many possible embodiments. Further, the same reference numbers in different drawings can identify the same or similar elements.

The invention claimed is:

1. A method of training a model for estimating likelihood of fatigue in test drivers, the method comprising:
   identifying, by one or more processors, training data including videos of the test drivers while such test drivers are tasked with monitoring driving of a vehicle operating in an autonomous driving mode, wherein the training data also includes driver drowsiness values generated from one or more human operators observing the videos as well as any fatigue events associated with the videos, wherein a fatigue event corresponds to a given test driver becoming distracted, closing eyes for more than a predetermined period, or falling asleep; and
   using, by the one or more processors, the training data to train the model such that when a new video of a first test driver is input into the model, the model will output an estimate of a likelihood of fatigue for the first test driver as well as a likelihood of the first test driver experiencing a future fatigue event.

2. The method of claim 1, wherein the training data further includes data corresponding to options selected by the one or more human operators observing the videos, wherein the options identify behaviors of test drivers related to fatigue.

3. The method of claim 2, wherein the options further identify whether test drivers are observing policies related to distractedness of test drivers.

4. The method of claim 3, wherein the policies include at least one policy relating to using a cell phone.

5. The method of claim 3, wherein the policies include at least one policy relating to keeping hands on a steering wheel.

6. The method of claim 1, further comprising:
   receiving user input corresponding to an abstract position on a sliding scale of driver drowsiness assessments; and
   converting the user input to one of the driver drowsiness values, wherein the one of the driver drowsiness values is a numerical value.

7. The method of claim 1, wherein each driver drowsiness value is associated with a reliability score, and wherein the model is further trained in order to provide a reliability score for the estimated likelihood of fatigue for the first test driver.

8. The method of claim 1, wherein the training data further includes intervention responses associated with the videos, each intervention response corresponding to an action to be taken in order to prevent a respective one of the fatigue events, and the model is further trained to provide a recommended intervention response for the first test driver.

9. A system for estimating likelihood of fatigue in test drivers, the system comprising one or more processors configured to:
   receive a video of a first test driver tasked with monitoring driving of a vehicle operating in an autonomous driving mode;
   input the video into a model in order to identify an estimated likelihood of fatigue for the first test driver;
   use the model to determine a reliability score for the estimated likelihood of fatigue; and
   send the video to be reviewed by one or more human operators based on the likelihood of fatigue for the first test driver and the reliability score.

10. The system of claim 9, wherein the one or more processors are further configured to
    determine a number of human operators for cross-validating the model, wherein the video is sent for review based on the determined number of human operators.

11. The system of claim 10, wherein the one or more processors are further configured to determine the number of human operators for cross-validating the model further based on reliability scores associated with currently available human operators.

12. The system of claim 11, further comprising determining the reliability scores associated with the currently available human operators based on cross-validations by other human operators of videos observed by the currently available human operators.

13. The system of claim 9, wherein the model further identifies an intervention recommendation for preventing a fatigue event in the first test driver, and wherein the video is sent to be reviewed based on the intervention recommendation, wherein the fatigue event corresponds to a given test driver becoming distracted, closing eyes for more than a predetermined period, or falling asleep.

14. The system of claim 9, wherein the model further identifies a likelihood of the first test driver experiencing a future fatigue event, wherein a future fatigue event corresponds to a given test driver becoming distracted, closing eyes for more than a predetermined period, or falling asleep.

15. The system of claim 9, wherein the one or more processors are further configured to input historical information related to fatigue events or interventions to prevent fatigue events for the first test driver into the model in order to estimate the estimated likelihood of fatigue for that test driver.

16. A system for estimating likelihood of fatigue in test drivers, the system comprising one or more processors configured to:
receive a video of a first test driver tasked with monitoring driving of a vehicle operating in an autonomous driving mode;
input the video into a model in order to identify an estimated likelihood of fatigue for the first test driver;
use estimated likelihoods of fatigue for a plurality of test drivers to determine an average estimated likelihood of fatigue across the plurality of test drivers for a fleet of autonomous vehicles; and
compare the average estimated likelihood of fatigue to a maximum allowable fatigue threshold.

17. The system of claim 16, wherein the one or more processors are further configured to use the comparison to identify test drivers to be removed from the test drivers for the fleet of vehicles.

18. The system of claim 9, wherein the model is a machine-learned model.

19. The system of claim 16, wherein the one or more processors are further configured to:
and
send the video to be reviewed by one or more human operators based on the likelihood of fatigue for the first test driver.

20. The system of claim 19, wherein the one or more processors are further configured to:
use the model to determine a reliability score for the estimated likelihood of fatigue; and
determine a number of human operators for cross-validating the model, wherein the video is sent for review based on the determined number of human operators.

* * * * *